United States Patent
Hahn et al.

(10) Patent No.: US 8,242,314 B2
(45) Date of Patent: *Aug. 14, 2012

(54) METHOD AND APPARATUS FOR PRODUCING PURIFIED METHYL ISOBUTYL KETONE

(75) Inventors: Tristan Erich Hahn, Johannesburg (ZA); Johannes Jochemus Gildenhuys, Johannesburg (ZA); Braam Van Dyk, Sasolburg (ZA); James Christoffel Crause, Sasolburg (ZA); Paranjothi Moodliar, Johannesburg (ZA)

(73) Assignee: Sasol Technology (PTY) Limited, Johannesburg (ZA)

( * ) Notice: Subject to any disclaimer, the term of this patent is extended or adjusted under 35 U.S.C. 154(b) by 425 days.

This patent is subject to a terminal disclaimer.

(21) Appl. No.: 12/086,491

(22) PCT Filed: Nov. 27, 2006

(86) PCT No.: PCT/IB2006/054455
§ 371 (c)(1),
(2), (4) Date: May 14, 2010

(87) PCT Pub. No.: WO2007/069110
PCT Pub. Date: Jun. 21, 2007

(65) Prior Publication Data
US 2010/0222612 A1 Sep. 2, 2010

(30) Foreign Application Priority Data
Dec. 14, 2005 (ZA) .................................. 2005/10181

(51) Int. Cl.
*C07C 45/82* (2006.01)
*C07C 45/84* (2006.01)

(52) U.S. Cl. ...................................................... 568/388
(58) Field of Classification Search .................. 568/861, 568/862, 863
See application file for complete search history.

(56) References Cited

U.S. PATENT DOCUMENTS

| | | |
|---|---|---|
| 3,574,763 A | 4/1971 | Wollner et al. |
| 3,953,517 A | 4/1976 | Schmitt et al. |
| 2003/0065227 A1 | 4/2003 | Saayman et al. |

OTHER PUBLICATIONS

Onoue et al.; "Why Not Do It in One Step? The Case of MIBK", CHEMTECH, XP009084353, pp. 36-39, (1977).
Al et al.; "Process for Separating Methylisobutanone Synthesized From Acetone", Abstract of CN 1 331 070, XP-002435247, (2002).

*Primary Examiner* — Sikarl Witherspoon
(74) *Attorney, Agent, or Firm* — Finnegan Henderson Farabow Garrett & Dunner LLP

(57) ABSTRACT

This invention relates to a method of producing purified methyl isobutyl ketone (MIBK) comprising subjecting a feed stream containing MIBK and impurities to a first distillation procedure from which acetone is recovered and a bottom product containing MIBK and impurities is withdrawn. This bottom product is fed to a second distillation column, where a vapor overhead product is withdrawn, condensed and fed to an overhead liquid-liquid separator. Part of an organic phase from the overhead liquid-liquid separator is fed to the second distillation column and part is fed to a third distillation column. A vapor overhead product is withdrawn from the third column which is condensed in the same said condenser. The condensed product is fed to the same said overhead liquid-liquid separator, and purified MIBK is withdrawn from the third distillation column. This invention also relates to an apparatus used in such a method.

20 Claims, 2 Drawing Sheets

METHOD AND APPARATUS FOR PRODUCING PURIFIED METHYL ISOBUTYL KETONE

CROSS REFERENCE TO RELATED APPLICATIONS

Figure 1:
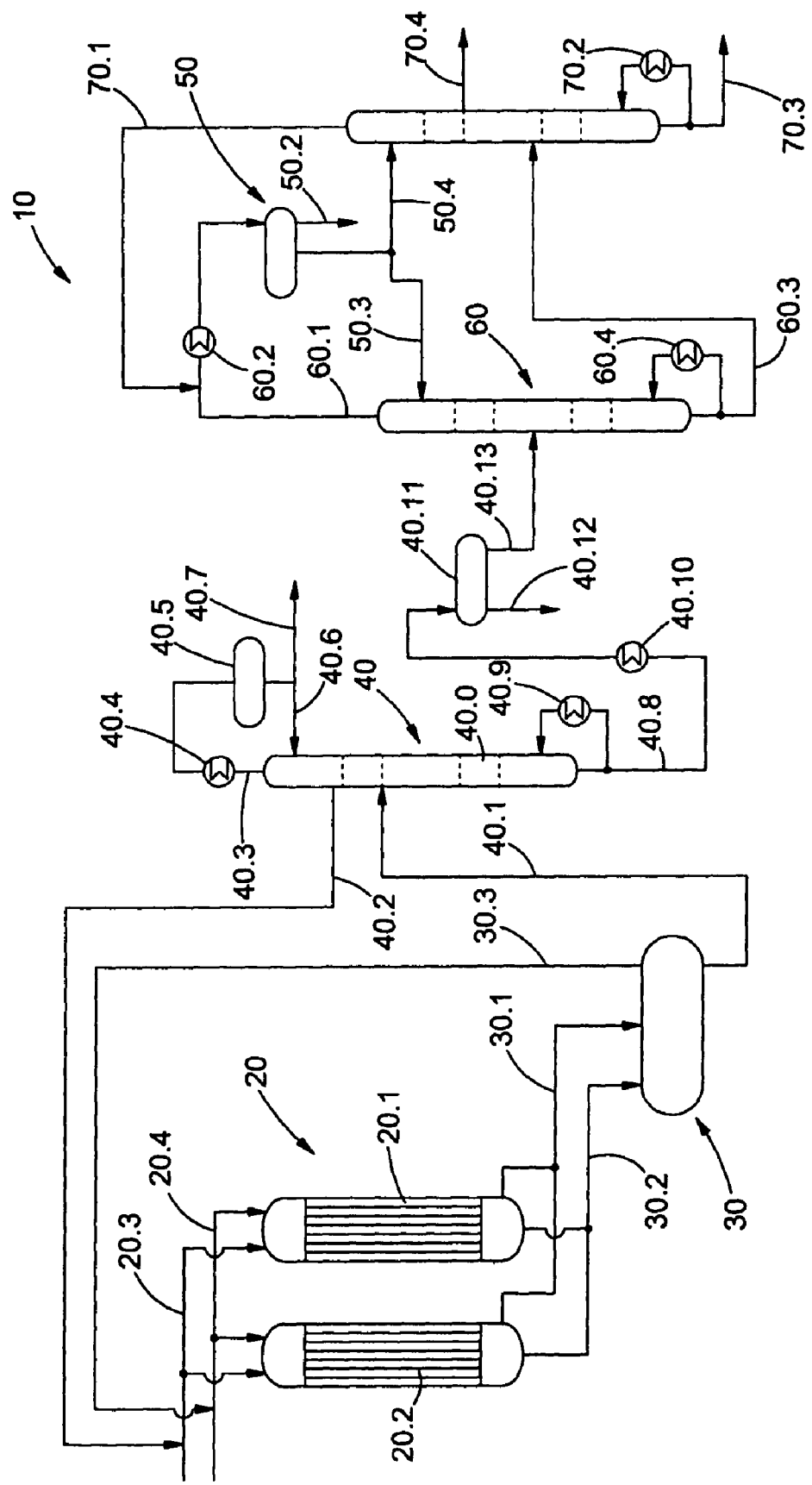

This application is a national phase application based on PCT/IB2006/054455, filed Nov. 27, 2006, and claims the priority of South African Application No. 2005/10181, filed Dec. 14, 2005, the content of both of which is incorporated herein by reference.

TECHNICAL FIELD

This invention relates to a method producing purified methyl isobutyl ketone (MIBK). The invention also relates to an apparatus for use in such a method.

BACKGROUND ART

Processes which include condensation of one or more carbonyl-containing reactants to form an unsaturated carbonyl-containing compound, and hydrogenation of said unsaturated compound to a saturated carbonyl-containing product, are well known.

One such process is the preparation of methyl isobutyl ketone (MIBK) from acetone. In this process condensation of two acetone molecules yield diacetone alcohol (DAA) which is dehydrated to yield mesityl oxide (MSO), and the MSO is hydrogenated to MIBK. The condensation and dehydration reaction takes place in the presence of an acidic catalyst, and the hydrogenation takes place in the presence of a hydrogenation catalyst such as a noble metal.

The production of MIBK can take place in two process steps as indicated above or in a single process step in the presence of a single condensation and hydrogenation catalyst. Such single step processes are disclosed in, for example, U.S. Pat. No. 3,574,763; EP 1 32 1 450 and South African complete patent application number 2004/8988.

The MIBK produced from the condensation and hydrogenation of acetone includes one or more impurities such as propane, isobutane, methyl pentane, acetone, 2-propanol, water, diacetone alcohol (DAA), mesityl oxide (MSO) and high boiling compounds such as diisobutyl ketone, C9 paraffins and ketones.

Methods of purifying MIBK are also known in the art. The article "Why not do it in one step", Chemtech, January 1977 discloses a process wherein the MIBK reaction products are subjected to a gas separator to remove unreacted hydrogen for recycle to the MIBK reactor. The liquid from the gas separator is fed to a first distillation column where acetone is recovered as an overhead product and recycled to the MIBK reactor. The bottom product of the first column is then fed to a liquid-liquid separator (decanter), where the aqueous phase is removed and the organic phase is fed to a second distillation column somewhere between the take-off of the bottom product and a reflux entry position. An overhead low boiling product is removed as distillate in the second column. The bottom product of the second column is then fed to a third distillation column where high boiling compounds are removed as the bottom product and MIBK is removed as the distillate.

"Methyl Isobutyl Ketone by Direct Condensation of Acetone", SRI Reports, May 1972, discloses a similar process as described above. The main difference is that the first distillation column described above is replaced by two columns, namely a first distillation column where low boiling products (particularly methyl pentane as an azeotrope with acetone) are removed as a distillate. The bottom product is then fed to a second column where the unreacted acetone is removed as a distillate and recycled to the MIBK reactor. Another difference is that the third column (similar function as the second column above) is fitted with an overheads decanter.

In the present invention there is provided a method and apparatus for producing and/or purifying MIBK wherein an at least partly shared overhead system between two distillation columns is provided.

DISCLOSURE OF THE INVENTION

Method

According to a first aspect of the present invention there is provided a method of producing purified methyl isobutyl ketone (MIBK) comprising:

subjecting a feed stream containing MIBK and impurities in the form of at least water and organic compounds (including unreacted acetone) from a condensation and hydrogenation reaction of acetone to a first distillation procedure from which at least acetone is recovered and a bottom product containing MIBK and impurities is withdrawn;

feeding the bottom product of the first distillation procedure to a second distillation column; withdrawing a vapour overhead product from the second distillation column; condensing the said overhead product in a condensor; feeding the resulting condensed overhead product to an overhead liquid-liquid separator wherein an organic phase and an aqueous phase separate; and feeding part of the organic phase from the overhead liquid-liquid separator to the second distillation column;

feeding part of the organic phase from the overhead liquid-liquid separator to a third distillation column; withdrawing a vapour overhead product from the third column which is condensed in the same condensor utilised for condensing vapour overhead product from the second distillation column, and fed to the overhead liquid-liquid separator (to which the condensed overhead product of the second distillation column is also fed); and withdrawing purified MIBK from the third distillation column.

The method may also include a step of producing MIBK, preferably by condensation and hydrogenation of acetone to provide the feed stream containing MIBK and impurities in the form of at least water and organic compounds (including unreacted acetone).

MIBK Production

The MIBK may be produced by any known process, but preferably it is produced in the presence of a single condensation and hydrogenation catalyst (e.g. a palladium based resin catalyst) preferably in a single process step. The MIBK may be produced as described in South African complete patent application number 2004/8988. The MIBK may be produced by feeding acetone and hydrogen to a suitable reactor such as a tubular reactor, preferably a tubular trickle bed reactor.

Hydrogen Removal

The method may also include a step of removing hydrogen from the feed stream containing MIBK and impurities from the condensation and hydrogenation reaction of acetone. The hydrogen will usually be unreacted hydrogen from the condensation and hydrogenation of acetone to produce MIBK.

The hydrogen may be removed at any suitable stage, preferably prior to the first distillation procedure. The hydrogen may be removed by means of a hydrogen separator, preferably a hydrogen separation drum, and the removed hydrogen may be recycled to the MIBK production step.

First Distillation Procedure

The first distillation procedure may be carried out in one or more distillation columns and preferably low boiling impurities are withdrawn separately from recovered acetone. Preferably the first distillation procedure is carried out in a single first distillation column by feeding the feed stream containing MIBK and impurities to the first distillation column wherein low boiling impurities are withdrawn as an overhead product; acetone is withdrawn as a side draw, and MIBK and impurities are withdrawn as a bottom product.

The overhead product of this column will usually contain compounds such as propane, isobutane, methyl pentane and some acetone. The overhead product may be refluxed. In one embodiment of the invention the overhead product may be condensed and may be fed to a reflux drum from which some overhead product is refluxed and some is discharged.

The acetone recovered (preferably as a side draw) may be recycled to the MIBK production step.

The withdrawn bottom product usually contains MIBK and high boiling impurities. The impurities may include acetone, 2-propanol, water and higher boiling compounds. The MIBK content at this stage may be in the region of 80 wt %.

The Second Distillation Column

The bottom product of the first distillation column may first be fed to a second or bottom liquid-liquid separator wherein an organic phase and an aqueous phase separates; and the organic phase may then be fed to the second distillation column. The aqueous phase from the bottom liquid-liquid separator may be withdrawn, may be discharged and may be fed to a water recovery unit.

Preferably the bottom product of the first distillation procedure is cooled prior to being fed to the bottom liquid-liquid separator.

The bottom liquid-liquid separator may comprise a decanter.

As stated before, the overhead product of the second column is condensed, and it may be sub-cooled, preferably in a condenser, prior to feeding it to the overhead liquid-liquid separator.

The organic phase of the overhead liquid-liquid separator fed to the second distillation column may be fed as reflux to the top region of the second column. The aqueous phase from the overhead liquid-liquid separator may be withdrawn, may be discharged and may be fed to a water recovery unit.

The overhead liquid-liquid separator may comprise a decanter.

It will be appreciated that the bottom liquid-liquid separator will withdraw some water and organic compounds (such as acetone and propanol) in the aqueous phase.

It will also be appreciated that the remaining acetone, 2-propanol, water in the organic phase of the bottom liquid-liquid separator fed to the second column, and some MIBK will usually report to the overhead product of the second column as a heterogeneous azeotrope. The organic phase of the overhead liquid-liquid separator is then refluxed to the second and third columns to recover the MIBK. The acetone and 2-propanol primarily report to the aqueous phase of the overhead liquid-liquid separator.

A light product purge may be withdrawn from the organic phase of the overhead liquid-liquid separator, and said purge may be recycled to the first column to recover acetone.

The bottom product of the first distillation procedure, or the organic phase from the bottom liquid-liquid separator may be fed to the second distillation column at a position between a reflux feed position and a bottom product withdrawal position.

Third Distillation Column

The organic phase of the overhead liquid-liquid separation fed to the third distillation column may be fed as reflux to the top region of the third column.

The overhead product of the third column may include MIBK and light decomposition products.

FIRST PARTICULAR EMBODIMENT

In one particular embodiment of the invention a bottom product containing MIBK and high boiling impurities may be withdrawn from the bottom of the second distillation column; the said bottom product is then fed to the third distillation column; high boiling impurities are withdrawn as a bottom product from the third distillation column; and purified MIBK is withdrawn as a side draw from the third distillation column.

The bottom product withdrawn from the bottom of the second distillation column is preferably fed to the third distillation column at a position between a reflux feed position and a bottom product withdrawal position.

Preferably the purified MIBK is withdrawn as a side draw in the third column in the rectification section thereof. The MIBK may have a purity of at least 99.5 wt %.

The bottom product of the third column contains high boiling impurities and may be treated as waste product.

SECOND PARTICULAR EMBODIMENT

In another embodiment of the invention high boiling impurities may be withdrawn as a bottom product from the bottom of the second distillation column. This bottom product may be removed from the system. It will be appreciated that the conditions in the second column should be such that a major portion (and preferably as much as possible) MIBK reports to the overhead product and accordingly a minor portion (preferably little as possible) MIBK reports to the bottom product.

In this case the purified MIBK may be withdrawn as a bottom product from the bottom of the third distillation column. Alternatively the purified MIBK may be withdrawn as sidedraw, preferably in the stripping section of the third distillation column, and high boiling compounds may be removed as a bottom product from the third distillation column.

Apparatus

According to a second aspect of the present invention there is provided apparatus suitable for producing purified methyl isobutyl ketone (MIBK) comprising:

a first distillation apparatus which includes a feed line for feeding a feed stream containing MIBK and impurities in the form of at least water and organic compounds (including acetone) from the condensation and hydrogenation reaction of acetone to the first distillation apparatus, the first distillation apparatus further including an acetone take-off for withdrawing acetone, and a bottom product take-off for withdrawing a bottom product in the form of MIBK and impurities from the bottom of the first distillation apparatus;

a feed line for feeding the bottom product of the first distillation apparatus to a second distillation column; an overhead vapour product take-off to withdraw a vapour overhead product from the second distillation column; a condensor for condensing the said overhead product from the second distillation column; a feed line for feeding the condensed overhead product to an overhead liquid-liquid separator wherein an organic phase and an aqueous phase in use separates; and a feed line for feeding part of the organic phase from the overhead liquid-liquid separator to the second distillation column; and a feed line for feeding part of the organic phase from the overhead liquid-liquid separator to a third distillation column; an overhead vapour take-off for withdrawing an overhead product from the third distillation column; a condensor for condensing the said overhead product (which is the same condensor utilised for condensing vapour from the second distillation column); a feed line for feeding the condensed overhead product to the overhead liquid-liquid separator (to which the condensed overhead product of the second distillation column is also fed); and a MIBK take-off for withdrawing purified MIBK from the third distillation column.

The apparatus may also include a reactor for producing MIBK, preferably by condensation and hydrogenation of acetone to provide the feed stream containing MIBK and impurities in the form of at least water and organic compounds (including acetone).

MIBK Reactor

The MIBK reactor may comprise any suitable MIBK reactor, preferably a reactor for producing MIBK in the presence of a single condensation and hydrogenation catalyst (e.g. a palladium based resin catalyst), preferably in a single process step. The MIBK reactor may comprise a tubular reactor, preferably a tubular trickle bed reactor with one or more feed lines for feeding acetone and hydrogen to the reactor.

Hydrogen Separator

The apparatus may also include means for removing hydrogen from the feed stream containing MIBK and impurities from the condensation and hydrogenation reaction of acetone. The means for removing hydrogen may comprise a hydrogen separator, preferably a hydrogen separator drum and may be located before the first distillation apparatus.

A hydrogen recycle feed line may be provided to feed the recovered hydrogen from the hydrogen separator to the hydrogen feed line to the MIBK reactor.

First Distillation Apparatus

The first distillation apparatus may comprise one or more distillation columns and preferably it includes an overhead product take-off for withdrawing low boiling impurities separately from the acetone take-off. Preferably the first distillation apparatus comprises a single first distillation column which preferably includes the feed line for the feed stream containing MIBK and impurities; an overhead product take-off for withdrawing low boiling impurities; an acetone take-off for withdrawing acetone as a side draw; and a bottom product take-off for withdrawing a bottom product in the form of MIBK and impurities.

The first distillation apparatus may also include a condensor for condensing the overhead product. The first distillation apparatus may also include a reflux drum for receiving the condensed overhead product, and a feed line for feeding at least part of the condensed overhead product from the reflux drum as reflux to the first distillation apparatus. The reflux drum may also include a discharge line for discharging at least some of the condensed overhead product from the reflux drum.

The first distillation apparatus may include a recycle line for recycling acetone withdrawn from the first distillation column to the MIBK reactor.

Second Distillation Column

The feed line for feeding the bottom product of the first distillation apparatus to the second distillation column may include a second or bottom liquid-liquid separator wherein an organic phase and a aqueous phase in use separates; and the liquid-liquid separator including a take-off for withdrawing and feeding the organic phase from the bottom liquid-liquid separator to the second distillation column. The bottom liquid-liquid separator may also include a take-off for withdrawing the aqueous phase.

The feed line to the bottom liquid-liquid separator may include a cooler for cooling the bottom product of the first distillation column prior to being fed to the bottom liquid-liquid separator.

The bottom liquid-liquid separator may comprise a decanter.

The overhead liquid-liquid separator may comprise a decanter.

The feed line for feeding the organic phase from the overhead liquid-liquid separator to the second column preferably feeds the said organic phase of the liquid-liquid separator as reflux to the top region of the second column. The overhead liquid-liquid separator may also include a take-off for withdrawing the aqueous phase.

The overhead liquid-liquid separator may also include a light product purge take-off for withdrawing a light product purge from the organic phase; and the said take-off may also include a recycle line for recycling the purge, preferably to the first column.

Third Distillation Column

The feed line for feeding part of the organic phase of the overhead liquid-liquid separator to the third column preferably feeds the said part of the organic phase to a reflux feed position on the third column.

FIRST PARTICULAR EMBODIMENT

In one particular embodiment of the invention the second column may include a bottom product take-off for withdrawing a bottom product in the form of MIBK and high boiling impurities from the bottom of the second column; a feed line for feeding said bottom product to the third distillation column; a bottom product take-off for withdrawing high boiling impurities from the bottom of the third distillation column; and a MIBK take-off for withdrawing purified MIBK as a side draw from the third distillation column.

The feed line for feeding the bottom product to the third column preferably feeds the bottom product to the third column at a position between a reflux feed position and a bottom product withdrawal position.

SECOND PARTICULAR EMBODIMENT

In another embodiment of the invention the second distillation column may include a bottom product take-off for withdrawing and removing a high boiling product from the bottom of the second column.

In this case the third column may include a MIBK take-off for withdrawing MIBK as a bottom product. Alternatively the third column may include a MIBK take-off for withdrawing MIBK as a sidedraw, preferably in the stripping section of the third distillation column; and preferably the third column includes a bottom product take-off for withdrawing a high boiling product from the bottom of the third column.

EXAMPLE

Figure 2:
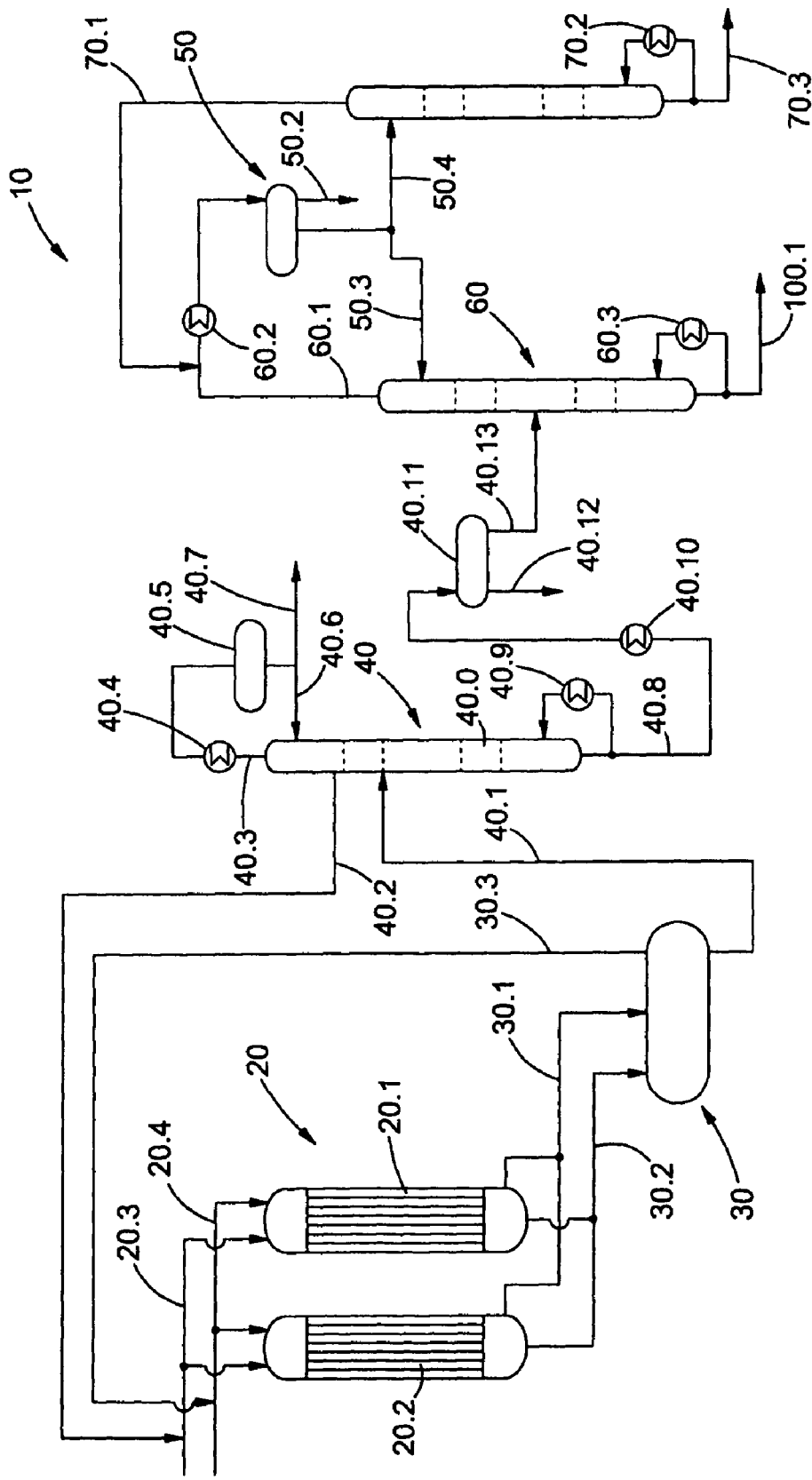

The invention will now be further described by means of the following non-limiting examples wherein:

FIG. 1 is a diagrammatic representation of an apparatus for producing purified MIBK according to a first embodiment of the present invention; and FIG. 2 is a diagrammatic representation of an apparatus for producing purified MIBK according to a second embodiment of the present invention.

Referring now to FIGS. 1 and 2 the apparatus 10 and 100 for producing purified MIBK comprises a reactor 20 for producing MIBK by condensation and hydrogenation of acetone; a hydrogen separator 30; a first distillation apparatus 40; an overhead liquid-liquid separator 50; a second distillation column 60 and a third distillation column 70.

The reactor 20 for producing MIBK comprises two tubular trickle bed reactors 20.1 and 20.2 for producing MIBK from acetone and hydrogen in the presence of a single condensation and hydrogenation catalyst (e.g. a palladium based resin catalyst) and in a single step. The reactors 20.1 and 20.2 include an acetone feed line 20.3 and a hydrogen feed line 20.4.

Vapour product from the reactors 20.1 and 20.2 are fed to the hydrogen separator 30 via feed line 30.1 while liquid product from the reactors 20.1 and 20.2 are fed to the hydrogen separator 30 via feed line 30.2. The hydrogen separator 30 comprises a hydrogen separation drum. A hydrogen recycle feed line 30.3 feeds recovered hydrogen to the hydrogen feed line 20.4.

The MIBK reactor 20 and hydrogen separator 30 are well known in the art and accordingly are not described in detail in this specification. The MIBK reactors 20.1 and 20.2 may be operated at 120° C. and 30 barg (3000 kPa).

The first distillation apparatus 40 comprises a single first distillation column 40.0 and includes a feed line 40.1 for feeding the product from the hydrogen separator 30 to the first column 40.0. The product in the feed line 40.1 in use contains MIBK and impurities in the form of at least water and organic compounds. The organic compounds comprise organic compounds (including unreacted acetone) from the condensation and hydrogenation reaction of acetone.

The first distillation column 40.0 also includes an acetone take-off 40.2 for withdrawing acetone as a side draw from the rectification section of the column. The acetone take-off 40.2 also serves as a recycle line for recycling the recovered acetone to the acetone feed line 20.3.

The first distillation column 40.0 further includes an overhead product take-off 40.3 for withdrawing low boiling impurities separately from the acetone take-off 40.2. The vapour overhead product take-off 40.3 feeds the overhead product to a condenser 40.4 and the condensed overhead product is then fed to a reflux drum 40.5 from which some of the condensed overhead product is refluxed via feed line 40.6 to the top region of the column 40.0 and some overhead product is discharged via line 40.7. The overhead product usually includes compounds such as propane, isobutane, methyl pentane and some acetone.

The first distillation column 40.0 also includes a bottom product take-off 40.8 for withdrawing a bottom product in the form of MIBK and impurities from the bottom of the first distillation column 40.0. The impurities may include acetone, 2-propanol, water and higher boiling compounds. The MIBK content at this stage may be in the region of 80 wt %. The column 40.0 is also equipped with a reboiler 40.9.

The bottom product take-off 40.8 is optionally fed to a cooler 40.10 prior to optionally being fed to the bottom liquid-liquid separator 40.11. If included the bottom liquid-liquid separator separates an organic phase and an aqueous phase. At least some acetone and 2-propanol will report to the aqueous phase. The aqueous phase is withdrawn and discharged through line 40.12 while the organic phase is withdrawn and fed to the second distillation column via line 40.13.

The bottom liquid-liquid separator 40.11 comprises a decanter.

The feed line 40.13 feeds the organic phase to the second column 60 at a position between a reflux feed position and a bottom product withdrawal position.

The second distillation column 60 includes an overhead take-off 60.1 for withdrawing a vapour overhead product. The take-off 60.1 feeds the overhead product to a condensor 60.2 which condenses the overhead product, and which condensed overhead product is then fed to the liquid-liquid separator 50.

It will be appreciated that acetone, 2-propanol, water and at least some MIBK will usually report to the overhead product of the column 60 as a heterogeneous azeotrope. The MIBK primarily reports to the organic phase of the decanter 50 which is refluxed to the columns 60 and 70, while acetone and 2-propanol primarily report to the aqueous phase of the liquid-liquid separator 50 which aqueous phase is discharged.

A light purge may be withdrawn [not shown] from the organic phase of the decanter 50 and it may be recycled to the first column 40.0 to recover acetone.

The overhead liquid-liquid separator 50 is a decanter. The aqueous phase from the decanter 50 is discharged through line 50.2 while the organic phase is fed as reflux to the second distillation column 60 via line 50.3 and as reflux to the third distillation column 70 via line 50.4.

The second column is fitted with a reboiler 60.3.

The third distillation column 70 includes an overhead product take-off 70.1 for withdrawing a vapour overhead product which is then fed to the condensor 60.2 from where it is fed with condensed overhead product of column 60 to the decanter 50.

The overhead product of the second column 60 includes mainly MIBK and light compounds.

The third column is fitted with a reboiler 70.2.

With reference to FIG. 1 only the second column 60 further includes a bottom product take-off 60.4 for withdrawing a bottom product in the form of MIBK and high boiling impurities from the bottom of the second column 60. The take-off 60.4 also serves as a feed line for feeding said bottom product to the third column 70.

The third distillation column includes a bottom product take-off 70.3 for withdrawing high boiling impurities from the bottom of the third column 70. A MIBK take-off 70.4 withdraws purified MIBK as a side draw from the rectification section of the column 70.

The feed line 60.4 feeds the bottom product from column 60 to a position between a reflux feed position and a bottom product withdrawal position.

With reference to FIG. 2 only, the second column 60 includes a bottom product take-off 100.1 for withdrawing and removing a bottom product from the bottom of the second column 60.

This bottom product may be removed from the system. It will be appreciated that the conditions in the second column is such that a major portion (and preferably as much as possible) MIBK reports to the overhead product and accordingly a minor portion (preferably little as possible) MIBK reports to the bottom product.

In this case the third column 70 includes a MIBK take-off 100.2 for taking off MIBK as a bottom product.

The following table illustrates typical stream temperature, pressure and composition for the first embodiment of the invention, as shown in FIG. 1, for the situation where the feed phase separator (40.11) to the second column is not included:

|  | 40.13 | 60.1 | 50.3, 50.4 | 50.2 | 70.1 | 70.4 | 70.9 |
|---|---|---|---|---|---|---|---|
| Temperature (° C.) | 98 | 112 | 68 | 68 | 89 | 132 | 173 |
| Pressure (bar) | 2 | 1.5 | 1.5 | 1.5 | 1.5 | 1.5 | 1.5 |
| Components mass percent |  |  |  |  |  |  |  |
| Acetone | 2% | 11% | 17% | 11% | 44% | 0% | 0% |
| MIBK | 79% | 77% | 74% | 2% | 32% | 100% | 15% |
| Water | 16% | 9% | 5% | 85% | 13% | 0% | 0% |
| Other heavier components | 3% | 0% | 0% | 0% | 0% | 0% | 85% |
| Other lighter components | 1% | 3% | 4% | 3% | 11% | 0% | 0% |

1 Bar is equal to 100 kPa

The following table illustrates typical stream temperature, pressure and composition for the second embodiment of the invention, as shown in FIG. 2, for the situation where the feed phase separator (40.11) to the second column is not included:

|  | 40.13 | 60.1 | 100.1 | 50.3, 50.4 | 50.2 | 70.1 | 100.2 |
|---|---|---|---|---|---|---|---|
| Temperature (° C.) | 98 | 112 | 173 | 68 | 68 | 89 | 132 |
| Pressure (bar) | 2 | 1.5 | 1.5 | 1.5 | 1.5 | 1.5 | 1.5 |
| Components mass percent |  |  |  |  |  |  |  |
| Acetone | 2% | 11% | 0% | 17% | 11% | 44% | 0% |
| MiBK | 79% | 77% | 15% | 74% | 2% | 32% | 100% |
| Water | 16% | 9% | 0% | 5% | 85% | 13% | 0% |
| Other heavier components | 3% | 0% | 85% | 0% | 0% | 0% | 0% |
| Other lighter components | 1% | 3% | 0% | 4% | 3% | 11% | 0% |

1 Bar is equal to 100 kPa

The invention claimed is:

1. A method of producing purified methyl isobutyl ketone (MIBK) comprising:
subjecting a feed stream containing MIBK and impurities in the form of at least water and organic compounds (including unreacted acetone) from a condensation and hydrogenation reaction of acetone to a first distillation procedure from which at least acetone is recovered and a bottom product containing MIBK and impurities is withdrawn;
feeding the bottom product of the first distillation procedure to a second distillation column; withdrawing a vapour overhead product from the second distillation column; condensing said overhead product in a condensor; feeding the resulting condensed overhead product to an overhead liquid-liquid separator wherein an organic phase and an aqueous phase separate; and feeding part of the organic phase from the overhead liquid-liquid separator to the second distillation column;
feeding part of the organic phase from the overhead liquid-liquid separator to a third distillation column; withdrawing a vapour overhead product from the third column which is condensed in the same condensor utilised for condensing vapour overhead product from the second distillation column; and fed to the overhead liquid-liquid separator (to which the condensed overhead product of the second distillation column is also fed);
and withdrawing purified MIBK from the third distillation column.

2. The method of claim 1 which includes a step of producing MIBK by condensation and hydrogenation of acetone to provide the feed stream containing MIBK and impurities in the form of at least water and organic compounds (including unreacted acetone).

3. The method of claim 2 wherein the MIBK is produced in the presence of a single condensation and hydrogenation catalyst in a single process step.

4. The method of claim 1 which includes a step of removing hydrogen from the feed stream containing MIBK and impurities from the condensation and hydrogenation reaction of acetone.

5. The method of claim 4 wherein the hydrogen is removed prior to the first distillation procedure.

6. The method of claim 1 wherein the first distillation procedure is carried out in one or more distillation columns; and low boiling impurities are withdrawn separately from the recovered acetone.

7. The method of claim 6 wherein the first distillation procedure is carried out in a single first distillation column by feeding the feed stream containing MIBK and impurities to the first distillation column wherein low boiling impurities are withdrawn as an overhead product; acetone is withdrawn as a side draw; and MIBK and impurities are withdrawn as a bottom product.

8. The method of claim 7 wherein the overhead product is refluxed.

9. The method of claim 2 wherein the acetone recovered is recycled to the step of producing MIBK.

10. The method of claim 1 wherein the bottom product of the first distillation column is first fed to a bottom liquid-liquid separator wherein an organic phase and an aqueous phase separates; and the organic phase is then fed to the second distillation column.

11. The method of claim 1 wherein a bottom product containing MIBK and high boiling impurities is withdrawn from the bottom of the second distillation column; said bottom product is then fed to the third distillation column; high boiling impurities are withdrawn as a bottom product from the third distillation column; and purified MIBK is withdrawn as a side draw from the third distillation column.

12. The method of claim 1 wherein high boiling impurities are withdrawn as a bottom product from the bottom of the second distillation column.

13. The method of claim 12 wherein the purified MIBK is withdrawn as a bottom product from the bottom of the third distillation column.

14. The method of claim 12 wherein the purified MIBK is withdrawn as sidedraw from the third distillation column, and high boiling compounds are removed as a bottom product from the third distillation column.

15. An apparatus suitable for producing purified methyl isobutyl ketone (MIBK) comprising:
a first distillation apparatus which includes a feed line for feeding a feed stream containing MIBK and impurities in the form of at least water and organic compounds (including acetone) from the condensation and hydrogenation reaction of acetone to the first distillation apparatus, the first distillation apparatus further including an acetone take-off for withdrawing acetone, and a bottom product take-off for withdrawing a bottom product in the form of MIBK and impurities from the bottom of the first distillation apparatus;

a feed line for feeding the bottom product of the first distillation apparatus to a second distillation column; an overhead vapour product take-off to withdraw a vapour overhead product from the second distillation column; a condensor for condensing said overhead product from the second distillation column; a feed line for feeding the condensed overhead product to an overhead liquid-liquid separator wherein an organic phase and an aqueous phase in use separates; and a feed line for feeding part of the organic phase from the overhead liquid-liquid separator to the second distillation column; and a feed line for feeding part of the organic phase from the overhead liquid-liquid separator to a third distillation column; an overhead vapour take-off for withdrawing an overhead product from the third distillation column; a condensor for condensing said overhead (which is the same condensor utilised for condensing vapour from the second distillation column); a feed line for feeding the condensed overhead product to the overhead liquid-liquid separator (to which the condensed overhead product of the second distillation column is also fed); and a MIBK take-off for withdrawing purified MIBK from the third distillation column.

16. The apparatus of claim 15 which includes a reactor for producing MIBK by condensation and hydrogenation of acetone to provide the feed stream containing MIBK and impurities in the form of at least water and organic compounds (including acetone).

17. The apparatus of claim 16 wherein the MIBK reactor is a reactor for producing MIBK in the presence of a single condensation and hydrogenation catalyst in a single process step.

18. The apparatus of claim 15 which includes means for removing hydrogen from the feed stream containing MIBK and impurities from the condensation and hydrogenation reaction of acetone.

19. The apparatus of claim 15 wherein the first distillation apparatus comprises one or more distillation columns and includes an overhead product take-off for withdrawing low boiling impurities separately from the acetone take-off.

20. The apparatus of claim 19 wherein the first distillation apparatus comprises a single first distillation column which includes the feed line for the feed stream containing MIBK and impurities; an overhead product take-off for withdrawing low boiling impurities; an acetone take-off for withdrawing acetone as a side draw; and a bottom product take-off for withdrawing a bottom product in the form of MIBK and impurities.

* * * * *